US00PP20445P2

(12) United States Plant Patent

Hanes

(10) Patent No.: US PP20,445 P2

(45) Date of Patent: Oct. 27, 2009

(54) *PELARGONIUM* PLANT NAMED 'AMRI CRARED'

(50) Latin Name: *Pelargonium hortorum* (L.) *L'Hérit. ex Ait*

Varietal Denomination: Amri Crared

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 12/218,548

(22) Filed: Jul. 16, 2008

(51) Int. Cl.
*A01H 5/00* (2006.01)

(52) U.S. Cl. ..... Plt./330

(58) Field of Classification Search ..... Plt./330, Plt./325

See application file for complete search history.

*Primary Examiner*—June Hwu

(74) *Attorney, Agent, or Firm*—S. Matthew Edwards

(57) ABSTRACT

A new *Pelargonium* plant named 'Amri Crared,' particularly distinguished by the bold red flower color, vigorous and strong, yet round and semi-compact with good branching, and good garden performance.

1 Drawing Sheet

Latin name of the genus and species of the plant claimed: *Pelargonium hortorum* (L.) *L'Hérit. ex Ait.*

Varietal denomination: 'Amri Crared'.

BACKGROUND OF THE NEW PLANT

The present invention comprises a new *Pelargonium,* botanically known as *Pelargonium hortorum,* and hereinafter referred to by the variety name 'Amri Crared.'

'Amri Crared' is a product of a planned breeding program. The new cultivar 'Amri Crared' has a bold red flower color, is vigorous and strong, yet round and semi-compact, with good garden performance.

'Amri Crared' originated from a hybridization in a controlled breeding program in Gilroy, Calif. USA. The female parent was an unpatented hybrid seedling identified as '9779-1' with a dark red flower color. '9779-1' has darker red flowers and has a less compact plant habit than 'Amri Crared.'

The male parent was an unpatented hybrid seedling identified as '9368-1' with a violet flower color. '9368-1' has a different flower color, is a stronger, more vigorous plant, and is later to flower than 'Amri Crared.'

'Amri Crared' was selected as one flowering plant within the progeny of the stated cross in August 2004 in a controlled environment in Gilroy, Calif. USA.

The first act of asexual reproduction of 'Amri Crared' was accomplished when vegetative cuttings were propagated from the initial selection in August 2004 in a controlled environment in Gilroy, Calif. USA.

Horticultural examination of plants grown from cuttings of the plant initiated in August 2004 in Gilroy, Calif. USA and continuing thereafter, has demonstrated that the combination of characteristics as herein disclosed for 'Amri Crared' are firmly fixed and are retained through successive generations of asexual reproduction.

'Amri Crared' has not been observed under all possible environmental conditions. The phenotype may vary significantly with variations in environment such as temperature, light intensity and day length.

Plant Breeder's Rights for this cultivar were applied for in Canada on Aug. 23, 2007 and in Germany on Jul. 2, 2007. 'Amri Crared' has not been made publicly available more than one year prior to the filing of this application.

DESCRIPTION OF THE PHOTOGRAPH

The accompanying photographic drawings shows typical flower and foliage characteristics of 'Amri Crared' with colors being as true as possible with an illustration of this type. The photographic drawings show a flowering potted plant of the new variety, and a close-up of the flowers.

DETAILED BOTANICAL DESCRIPTION

The measurements were taken in Gilroy, Calif. USA, in August 2007 on plants that were growing in 16 inch containers, containing 3 plants each. Culture of these plants started in a greenhouse in April 2007 and were transferred to the outdoor containers in early June 2007. The plants were approximately 4 months old.

Color Chart used: The Royal Horticultural Society Colour Chart (R.H.S.) 2001

BRIEF SUMMARY OF INVENTION

The following observations, measurements, and comparisons describe plants grown outside in Gilroy, Calif. USA. The following traits have been repeatedly observed and are determined to be basic characteristics of the new variety. The combination of these characteristics distinguishes this *Pelargonium* as a new and distinct variety.

TABLE 1

DIFFERENCES BETWEEN THE NEW VARIETY 'AMRI CRARED' AND A SIMILAR VARIETY

| | 'Amri Crared' | 'Fisromag' (U.S. Plant Pat. No. 13,252) |
|---|---|---|
| Flower color: | Somewhat less bluish | More bluish |
| Leaf zone: | Somewhat stronger zonation | Less zonation |
| Plant vigor: | More vigorous plant | Less vigorous |

Plant:

*Form, growth and habit.*—Upright, and rounded growth habit. Vigorous, well-branched.
*Plant height* (*cm*).—12–14.
*Plant height* (*inflorescence included*)(*cm*).—22–23.
*Plant width* (*cm*).—22–25.

Foliage:

*Arrangement.*—Alternate, simple.
*Immature, leaf color, upper surface.*—RHS 137A.
*Lower surface.*—RHS 137C.
*Mature, leaf color, upper surface.*—RHS 137B.
*Lower surface.*—RHS 137C.
*Length* (*cm*).—4.0–4.5.
*Width* (*cm*).—6.7–7.2.
*Shape.*—Reniform.
*Base shape.*—Cordate.
*Apex shape.*—Rounded.
*Margin.*—Irregularly crenate.
*Texture, upper surface.*—Hirsute, few glandular hairs.
*Lower surface.*—Hirsute, few glandular hairs.
*Color of zone.*—Light hue of RHS 187A.
*Width of zone* (*cm*).—0.5–0.7.
*Color of veins, upper surface.*—RHS 146A.
*Color of veins, lower surface.*—About RHS 146B.
*Petioles color.*—RHS 146A.
*Petioles length* (*cm*).—5.3–5.6.
*Diameter of petiole* (*cm*).—0.25–0.3.
*Texture.*—Hirsute; glandular hairs.

Stem:

*Color of stem.*—RHS 144B.
*Length of stem* (*cm*).—5–7.
*Diameter* (*cm*).—0.9–1.1.
*Length of internodes* (*cm*).—1.0–1.5.
*Texture.*—Hirsute.

Inflorescence:

*Type.*—An umbel composed of 40–50 flowers and buds.
*Average quantity of umbels per plant.*—30–40.
*Umbel diameter* (*cm*).—9–10.
*Umbel depth* (*cm*).—5–6.
*Color of peduncle.*—RHS 144A.
*Length of peduncle* (*cm*).—12–13.5.
*Peduncle diameter* (*cm*).—0.4.
*Texture.*—Hirsute; pilose; some glandular hairs, some are RHS 24C.
*Color of pedicel.*—Some are RHS 178A and some are closer to RHS 187B.
*Length of pedicel* (*cm*).—2.2–2.6.
*Diameter of pedicel* (*cm*).—0.15.
*Texture.*—Many glandular hairs, some about RHS 24D.

Corolla:

*Form.*—Polypetalous, overlapping.
*Number of petals.*—9–11.
*Width of flower* (*cm*).—4.5–5.4.
*Depth of flower* (*cm*).—2.0–2.4.
*Color upper petals, upper surface.*—Closest to RHS 46B but a more velvety red; fades to about RHS 46B but with a more bluish hue; RHS 46A veins basally.
*Color upper petals, lower surface.*—RHS 45C.
*Length of upper petals* (*cm*).—2.4–2.5.
*Width of upper petals* (*cm*).—2.8–2.9.
*Color lower petals, upper surface.*—Closest to RHS 46B but a more velvety red; fades to about RHS 46B but with a more bluish hue.
*Color lower petals, lower surface.*—RHS 45C.
*Length of lower petals* (*cm*).—2.5–2.6.
*Width of lower petals* (*cm*).—1.7–1.8.
*Petal shape.*—Spathulate.
*Apex shape.*—Rounded.
*Margin.*—Entire.
*Petal texture.*—Papillose.
*Number of petaloids.*—Rarely 1–2.
*Average width of petaloids* (*cm*).—0.5.
*Average length of petaloids* (*cm*).—1.75.
*Color petaloids.*—Closest to RHS 46B but a more velvety red; fades to about RHS 46B but with a more bluish hue.
*Duration of flowering.*—Continuous flowering throughout the Summer.
*Lastingness of flowers.*—About one week.

Bud (just before opening):

*Color.*—RHS 46B.
*Length* (*cm*).—1.3–1.5.
*Width* (*cm*).—0.6–0.8.
*Shape.*—Ovoid.
*Number of sepals.*—5 fused at the base.
*Color of sepals.*—RHS 146C; anthocyanins of RHS 187A basally.
*Length of sepals* (*cm*).—1.0–1.2.
*Width of sepals* (*cm*).—0.3–0.5.
*Sepal shape.*—Ovate.
*Apex shape.*—Acute.
*Margins.*—Entire.
*Texture, upper surface.*—Smooth and glossy.
*Lower surface.*—Few pilose; glandular hairs.

Reproductive organs:

*Pistil.*—1.
*Length* (*cm*).—0.8–0.9.
*Style color.*—RHS 189B.
*Style length* (*cm*).—0.3.
*Stigma color.*—RHS 184B.
*Number of anthers.*—4–6.
*Color of filaments.*—RHS N155B but whiter basally, to about RHS 53B at apex.
*Length filaments* (*cm*).—0.5–0.8.
*Pollen amount.*—Moderate.
*Color of pollen.*—Between RHS 28A and RHS 32A.
*Fertility/seed set.*—Not observed on this hybrid.

Disease/pest resistance: Disease resistance and/or susceptibility has not been observed on this hybrid.

What is claimed is:

1. A new and distinct variety of *Pelargonium* plant named 'Amri Crared,' substantially as illustrated and described herein.

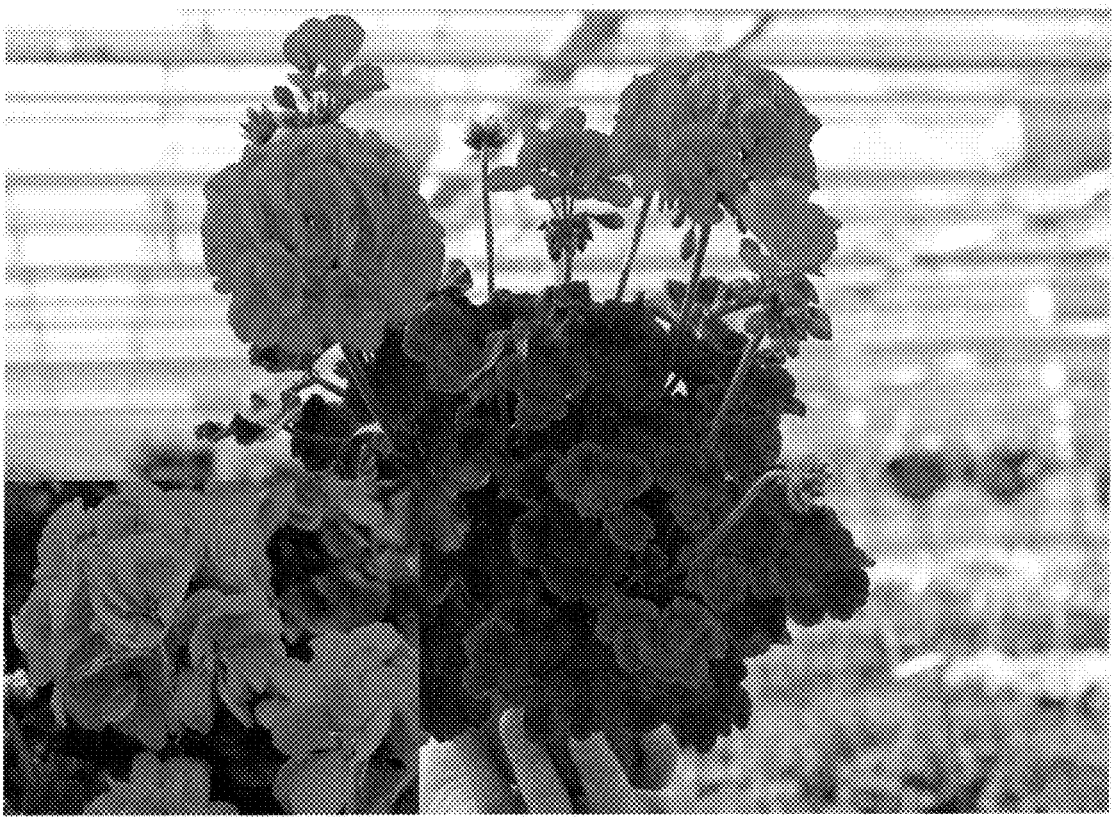

* * * * *